(12) United States Patent
Zawada

(10) Patent No.: US 6,592,611 B1
(45) Date of Patent: Jul. 15, 2003

(54) VIOLATION OF TIME REVERSAL INVARIANCE IN LIVING TISSUE

(76) Inventor: Robert H. Zawada, 81 Suburban Ct., W. Seneca, NY (US) 14224

( * ) Notice: Subject to any disclaimer, the term of this patent is extended or adjusted under 35 U.S.C. 154(b) by 0 days.

(21) Appl. No.: 09/686,011

(22) Filed: Oct. 10, 2000

(51) Int. Cl.⁷ .............................................. A61N 5/067
(52) U.S. Cl. ................. 607/89; 606/3; 606/11
(58) Field of Search ................ 606/2, 3, 10, 11; 607/89

(56) References Cited

U.S. PATENT DOCUMENTS

| | | | | |
|---|---|---|---|---|
| 4,930,504 A | * | 6/1990 | Diamantopoulos et al. | 606/3 |
| 4,931,053 A | * | 6/1990 | L'Esperance, Jr., | 606/10 |
| 4,966,144 A | * | 10/1990 | Rochkind et al. | 607/89 |
| 5,139,494 A | * | 8/1992 | Freiberg | 606/10 |
| 5,403,306 A | * | 4/1995 | Edwards et al. | 606/2 |
| 5,409,482 A | * | 4/1995 | Diamantopoulos | 606/10 |
| 5,445,146 A | * | 8/1995 | Bellinger | 606/3 |
| 6,063,108 A | * | 5/2000 | Salansky et al. | 606/13 |
| 6,086,580 A | * | 7/2000 | Mordon et al. | 606/3 |
| 6,290,714 B1 | * | 9/2001 | Streeter | 606/10 |

* cited by examiner

*Primary Examiner*—Michael Powell Buiz
*Assistant Examiner*—Ramesh Krishnamurthy
(74) *Attorney, Agent, or Firm*—Hugh D. Jaeger

(57) ABSTRACT

The present invention provides for a device, a method, and a treatment system for chronic disease conditions. The present invention was designed using the theoretical concepts of Quantum Biology. The principles of operation are based on the device's ability to stimulate a Bose-Einstein condensate and excitation of Frolich resonance in living tissue The wavenumbers necessary for this excitation are derived from the solution to the equations for optical phonon scattering in living tissue generated by optical photon excitation. The establishment of this degeneracy condition induces a super conducting state in the tissue. This super conducting state facilitates DNA replication, transcription and translation, thereby allowing the proper formation or regeneration of healthy tissue. This superconducting state provides the conditions necessary for establishing the violation of time reversal invariance in living tissue.

32 Claims, 2 Drawing Sheets

* CONTROL ELECTRONICS- USER ADJUSTABLE FOR THE FOLLOWING PARAMETERS:
POWER OUTPUT; MODULATION WAVEFORM (SINE, SQUARE, TRIANGULAR OR SAWTOOTH);
DUTY CYCLE; PULSE REPETITION RATE.

VIOLATION OF TIME REVERSAL INVARIANCE IN LIVING TISSUE

CROSS REFERENCES TO CO-PENDING APPLICATIONS

None.

BACKGROUND OF THE INVENTION

1. Field of the Invention

The present invention is for a violation of time reversal invariance in living tissue, and more particularly, pertains to a violation of time reversal invariance in living tissue by means of exogenously applied electromagnetic radiation with wavenumbers between k=33,333 cm$^{-1}$ to k=33,333 cm$^{-1}$.

The present invention is designed for use in non-invasive therapy. This is a non-invasive technique for the treatment of numerous chronic diseases and conditions, primarily arthritis, chronic pain from injuries, and wound healing, such as bed sores, decubitus, and diabetic ulcers.

2. Description of the Prior Art

The present invention specifically describes the mode of biophysical mechanisms of action, which has not been accomplished in any prior art or device.

Current U.S. standard and FDA approved treatments for the above mentioned chronic diseases and conditions include medication, surgery and physical therapy. Other existing therapies and therapy devices that are known in the world market attempt to treat described conditions with non-invasive electromagnetic radiation applications, but lack an accurate explanation of a mechanism of action. Therefore, they are unable to maximize their efficiency.

SUMMARY OF THE INVENTION

The general purpose of the present invention is to provide a non-invasive treatment of disease conditions such as arthritis; healing of wounds, and soft tissue injuries, i.e. sports injuries; and relief from chronic conditions, such as Carpal Tunnel Syndrome and chronic ulcers.

The present invention is intended for use in general medical practice. The use of the present invention will, in many cases, eliminate the need for medication, physical therapy, surgery, and ongoing patient care.

The present invention also provides a treatment system for chronic disease conditions. The present invention is based upon application of the theoretical concepts of Quantum Biology to a variety of disease and chronic conditions. The principles of operation are based on stimulating the production of a Bose-Einstein condensate in living tissue The wavenumbers necessary for this excitation are derived from the solution to the equations for optical phonon scattering in living tissue generated by optical photon excitation. The establishment of this degeneracy condition induces a superconducting state in the tissue providing the appropriate instruction set for correct DNA replication, transcription and translation. Thus, allowing the proper formation or regeneration of healthy tissue.

Electromagnetic frequencies excite ordered water around proteins at about 10⁻Hz. The present invention is based upon excitation of the Frohlich resonant frequencies in human tissue. Resonant energy transfer, generated by photon excitation at specific wavelengths of 655 nm and 1060 nm generate Brillouin scattered phonons at $0.424 \times 10^{11}$ Hz and $0.262 \times 10^{11}$ Hz, respectively. These frequencies establish a Bose-Einstein condensate within the living tissue. The ratio of 1060 nm/655 nm=1.618 which is the golden mean ratio and known to be biologically active. 655 nm is the solution to the Balmer series equation for the first line of hydrogen emission. Biological tissue involves extensive hydrogen bonding. The dimensional resonance of DNA is also known to be 34 Å/21 Å≈1.618 for efficient energy transfer from the golden mean ratio. 655 nm is also the main absorption band of Heat Shock Protein 47 (HSP47), which is the chaperon for collagen synthesis. The use of multiple wavelengths at the golden mean ratio provide a synergistic effectiveness.

If we start with the first line of the Balmer Series for hydrogen:

$\lambda(B)=3646(N^2/N^2-4)$ for $N=3$ $\lambda(B)=656.28$ nm $\lambda(B)\approx655$ nm Therefore, this 655 nm becomes the primary absorption wavelength in this invention. The Frohlich resonance of ordered water around proteins is $\approx 10^{14}$ Hz. The optical excitations at 655 nm and 1060 nm both provide excitation in this band.

Electromagnetic radiation coherently excites the ordered water molecules, which in turn excite tunneling through the creation of evanescent photons in the nucleotide bonds. The Frohlich resonance is a non-local effect occurring in the water surrounding and in the core of the microtubules connecting all cellular structure. Excitations at a frequency of $10^{14}$ Hz, excites the water surrounding the protein structure and a frequency of $10^{14}$ Hz, excites water in the core of the protein structure of the microtubules. This in turn generates a collective and cooperative behavior of a great number of the constituents, known in Quantum Mechanics as the degeneracy state, or multiples of identical quantum numbers. This can then be associated with a non-local long range order, in which information is transmitted in the superconducting state. This long range transfer is established through longitudinal electric modes in the microtubules and generates a single quantum state. If energy is fed into these modes and transferred to other degrees of freedom, then a stationary state will be reached where the energy content of the electric mode is larger than thermal equilibrium. A coherent electric wave is then channeled into a single mode. The local vibrations of the cell membrane then create a positive and negative part of particular sections of the membrane that vibrate against each other leading to an oscillating electric dipole frequency of the order of $10^{11}$ Hz.

The hydrogen bonds have distinctive dipolar properties. The alpha helix is expected to exhibit collective dipole oscillations in the same frequency region, and also from non-localized electrons in this region of the cell.

The dielectric systems have a certain range of macroscopic wavelengths capable of longitudinal electric oscillations over the whole material. Processes involving cell membrane or H-bonds are expected to feed energy locally to particular dipole oscillators. Long range coulomb interactions can cause energy to be shared with other dipoles that will oscillate coherently provided energy supply is sufficient and a single longitudinal mode can exhibit long range phase correlations. Since biological tissue exhibits very wide absorption bands, optical excitation ranging from the UVA to the near IR can stimulate biological activity.

The purpose of the present invention is to maximize this biological activity, even though a broad spectral range can still exhibit stimulatory effects. The free energy associated with vibration can be decreased if the system is permitted to undergo deformations or interactive decoherence. Therefore, coherence must be re-established. Relevant components can be connected with certain regions in the cell membrane by H-bonds. If energy is supplied locally (in regions containing non-localized electrons), then energy is shared by all components which establish a branch of electric modes. When cells are closely packed, deformations in the cell membrane will no longer influence the di-electric response, this is known as contact inhibition.

Coherent electromagnetic excitation presents a reservoir of energy and when the absorption of light is $\hbar w >> kT$ it can lead to energy storage in a single state. This coherently excites the ordered water molecules, which in turn excite the tunneling in the nucleotide bonds. When the conformational grooves of a protein are filled with water, the entire protein is in coherent vibration. This also applies to the B form of DNA, which is the hydrated form found in living organisms. Non-local effects such as remote triggering are expected whenever a very fast coupling (i.e., optical) occurs in a system with slow local dynamics (i.e., conformational changes in biological systems). Examples include biochemical processes coupled by electric field effects, such as are present in tissue. The force constant for dangling N—H bonds, such as that seen in nucleotide base pairs, is $8.955 \times 10^{13}; \approx 10^{14}$, which coincides with the Frohlich resonance in water, similar to the Meissner effect. The $v_3$ Raman resonance in water of $2.77\mu$ generates dipoles which in turn create ordered states. $2.77\mu$ coincides with the second harmonic golden mean overtone of the applied optical radiation at a wavelength of 1060 nm of Appendix A, incorporated herein by reference. The ordered water in microtubules then establishes Frohlich resonances from dipole and Vander Waal forces, creating a Bose-Einstein condensate.

The Bose-Einstein condensate creates non-local communication throughout microtubules and a re-coherence of cellular state.

The calculation of the appropriate optical phonons that are generated from the excitation by optical photons is as follows:

$$v = c/\lambda, w = 2\pi v$$

(where $v$=frequency of light, $\lambda$=wavelength of light $w$=angular frequency)

$$\Omega \approx 2 V_8 w(n/c)$$

(where $n=1.38$ in tissue $V_8$=velocity of sound in tissue $V_8=1600$ m/s in tissue $\Omega$=optical phonon frequency)

$$= 2V_8 2\pi n/\lambda$$

$$= 2(1.6 \times 10^3)(2\pi)(1.38/1060 \times 10^{-9})$$

$$\Omega(1060 \text{ nm}) = 0.261759 \times 10^{11} \text{ Hz}$$

$$\Omega(655 \text{ nm}) = 0.42361 \times 10^{11} \text{ Hz}$$

These numbers fall exactly into the biologically active region for Frohlich resonance. Specifically, for H-bonds, this combination will generate maximum effectiveness because of their efficient coupling for energy to H-bonds for phonon excitation and to water for photon excitation.

$$v = c/\lambda$$

$$v_{1060} 3 \times 10^8 \text{ m/s}/1.06 \times 10^{-6} \text{ m} = 2.83 \times 10^{14} \text{ Hz}$$

$$v_{655} = 3 \times 10^8 \text{ m/s}/0.655 \times 10^{-6} \text{ m} = 4.5 \times 10^{14} \text{ Hz}$$

Although some biological activity will be seen in the band with from 300 nm to $3\mu$ and will be effective for the process of tissue regeneration, it will be optimized for wavelengths of 655 nm±100 nm; 1060 nm±100 mn; $2.77\mu$±100 nm.

New aspects of the present invention are the use of quantum biological principles to create the most effective treatment of diseased tissue. No other device or treatment method uses these principles. The wavelengths used give the best penetration depth into soft tissue and bone. 1060 nm is equally effective on all skin pigmentation, as well as $2.77\mu$. In other words, irrespective of the particular pigmentation pattern, quantity, or quality of a patient being treated, the 1060 nm coherent electromagnetic radiation employed in the present invention is particularly advantageous in penetrating beneath the patient's skin and interacting with underlying tissue. Wavelengths chosen maximize energy transfer to tissue for most effective regeneration of healthy tissue. The present invention is the only one based on the exact calculations of the frequencies to excite the Frohlich resonance.

The invention is the most effective device possible for stated application, due to the exact tuning of the emission frequencies.

Any method of generating coherent electromagnetic radiation at wavelengths in the spectral region of 300 mn to $3\mu$ is suitable for generating coherent electromagnetic radiation for the present invention, provided, of course, that the radiation must be at the specific wavelengths of the invention. The use of laser diodes is the most practical and cost effective means for producing the coherent electromagnetic radiation used in this invention, at the specific wavelengths indicated. It is within the skill of art to prepare a laser diode for generation of a designated wavelength.

Having thus described embodiments of the present invention, it is the principal object of the present invention to provide a violation of time reversal invariance in living tissue.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
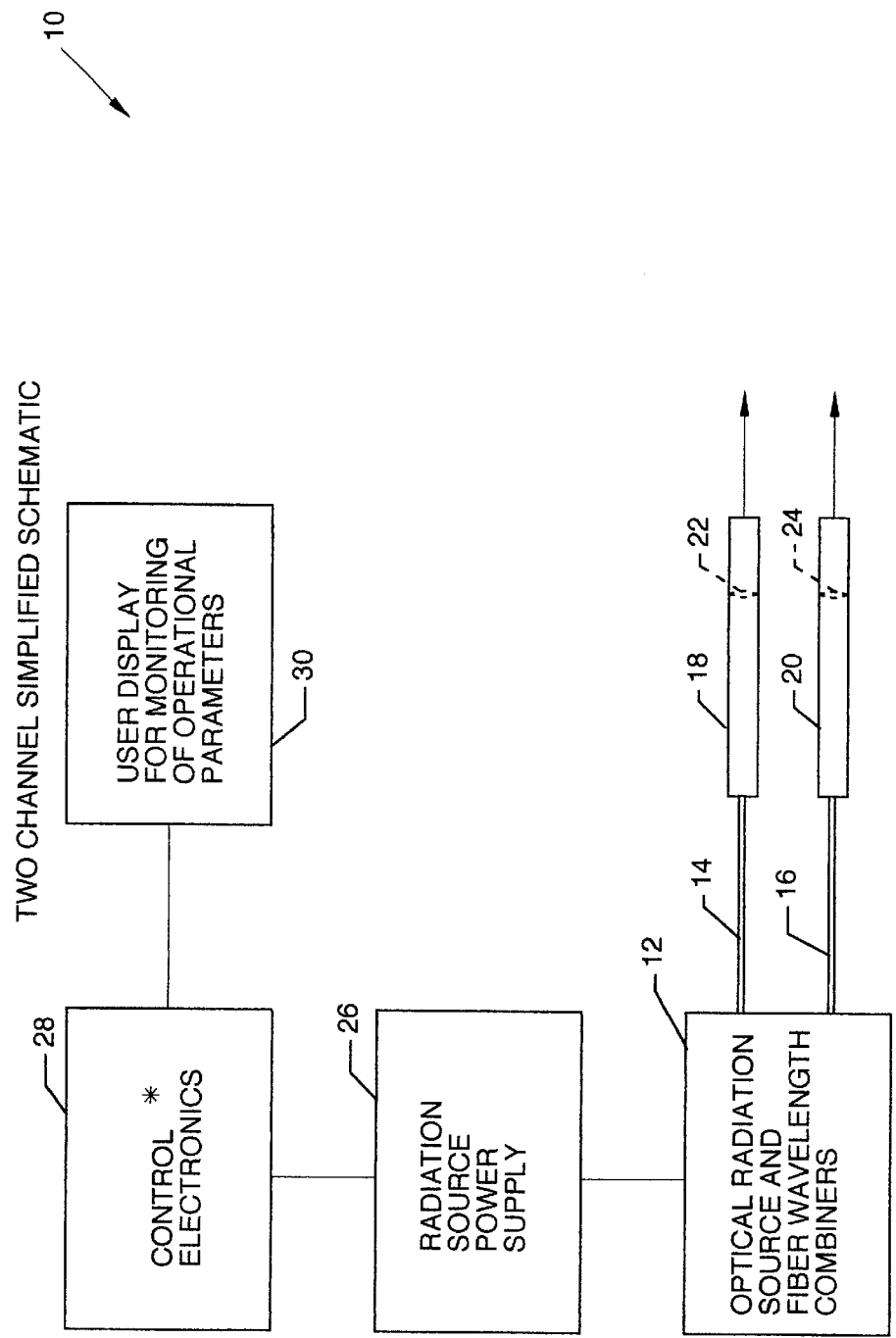
FIG. 1 illustrates an apparatus comprising the present invention.

FIG. 1 illustrates a two-channel simplified schematic of the present invention consisting of a diode laser module 12 in which the effective wavelengths of light are generated and combined fiber-optically for emission functioning as a combined single output. In other words, the combined single output includes a first coherent light at a first wavelength and a second coherent light at a second wavelength, different from the first wavelength. Optionally, a third, different wavelength of coherent light may also be present in the combined single output. The diode laser module 12 consists of at least two channels with identical multiple wavelengths emitted from each channel. In other words, the combined single output, having two or more different wavelengths of coherent light, is split into two or more channels, each channel identical in composition by virtue of consisting of two or more different wavelengths of coherent light. Each channel feeds into a separate fiber optic delivery system cables 14 and 16, probes 18 and 20 containing collimating focusing lenses 22 and 24. Also included are a radiation source power supply 26, control electronics 28, and a user display 30 for monitoring of operational parameters. Preferably, the probes 18 and 20 are handheld, but alternatively may be mechanically held in a desired orientation.

Figure 2:
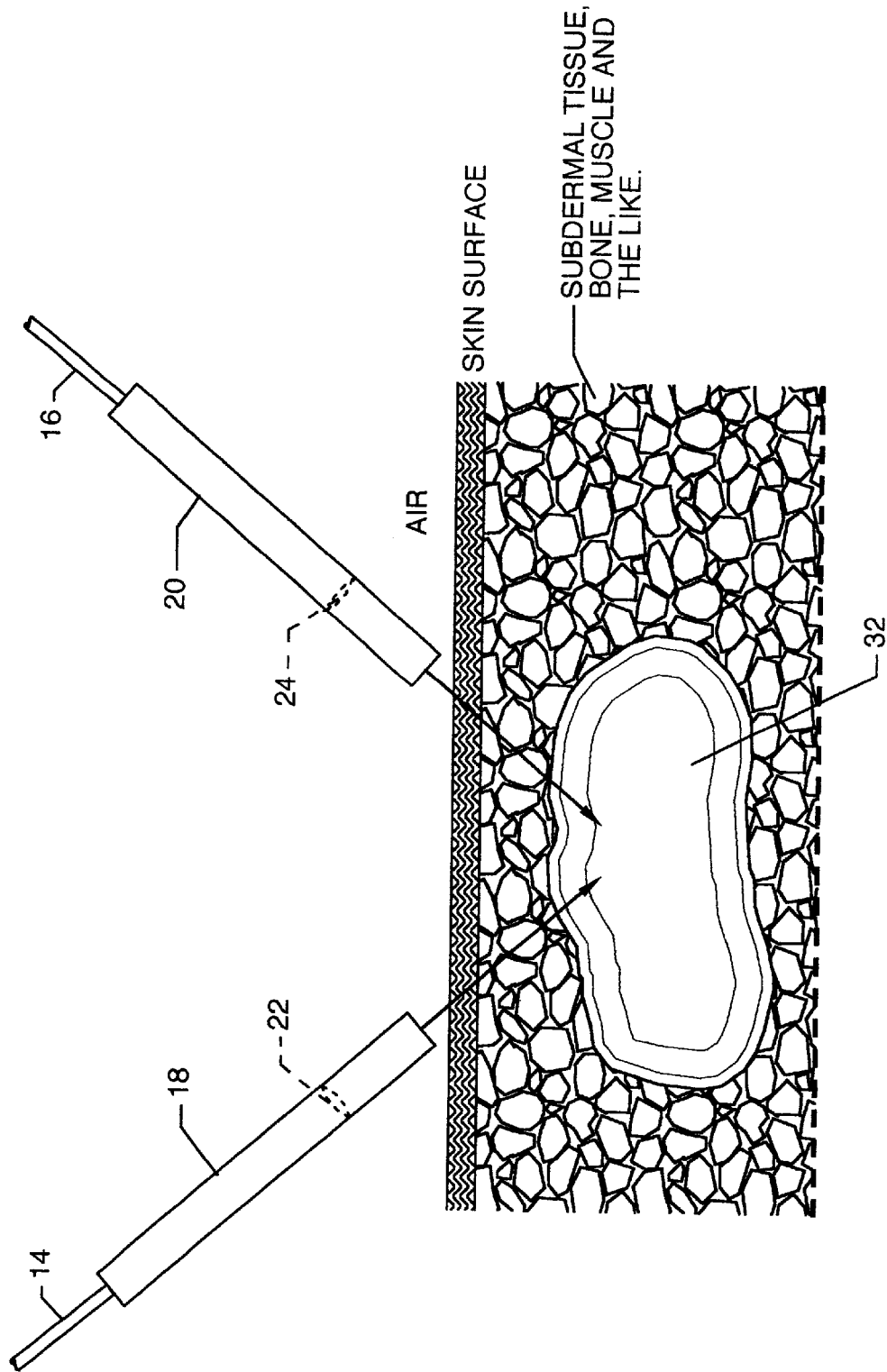
FIG. 2 illustrates handheld probes treating tissue by optical radiation.

FIG. 2 illustrates the preferred two or more handheld probes 18 and 20 for delivery of the optical radiation into the tissue. The purpose of the two or more probes 18 and 20 is to maintain a maximum power of 500 mw/cm² per probe, which is known to be a safe exposure to human skin. This gives the optical source a CDRH classification of IIIb. The probes 18 and 20 can be separately directed to a single treatment area 32 below the skin surface to maximize light below the skin surface without causing tissue damage at the air dermal interface.

MODE OF OPERATION

The mode of operation is based on the excitation of Frohlich resonance in the microtubule cytoskeletal substructure of the cell. This excitation creates a Bose-Einstein condensate in the microtubule and a degeneracy state for information transfer. The ability to establish this singular communication system within the cellular structure is what allows for the transfer of the information necessary to correct for DNA dysfunctions or mutations causing the diseased state.

Various modifications can be made to the present invention without departing from the apparent scope hereof.

What is claimed is:

1. A non-invasive method for treating living biological tissue characterized by a disease state, the method comprising the steps of:
   a. providing optical radiation consisting of a first coherent light having a wavelength which is a first Frohlich resonant frequency and a second coherent light having a wavelength which is a second Frohlich resonant frequency; and,
   b. applying the optical radiation to the biological tissue to be treated, and inducing a quantum degeneracy state so as to facilitate regeneration of the living biological tissue and reduction of the disease state.

2. The non-invasive method of claim 1, wherein the disease state characterizing the tissue to be treated is selected from the group consisting of arthritis, chronic pain, and ulcers.

3. The non-invasive method of claim 1, wherein the biological tissue to be treated is selected from the group consisting of soft tissue, bone, and collagen producing tissue.

4. The non-invasive method of claim 3, wherein the tissue to be treated includes Heat Shock Protein 47 (HSP47).

5. The non-invasive method of claim 1, wherein the biological tissue to be treated is sub-dermal tissue.

6. The non-invasive method of claim 1, wherein the biological tissue to be treated is dermal tissue.

7. The non-invasive method of claim 1, wherein the optical radiation originates in at least a first laser diode generating coherent light having a wavelength of about 655 nm±100 nm and at least a second laser diode generating coherent light having a wavelength of about 1060 nm±100 nm.

8. The non-invasive method of claim 1, wherein the optical radiation is applied to skin at a maximum power of 500 mw/cm².

9. The non-invasive method of claim 5, wherein the optical radiation is applied to a selected region of sub-dermal biological tissue to be treated by application of multiple distinct beams, each of the multiple distinct beams having a distinct path, a maximum power of 500 mw/cm², and being directed toward the selected region of sub-dermal biological tissue such that a higher combined power is provided in the selected region of sub-dermal biological tissue.

10. The non-invasive method of claim 9, wherein each of the multiple distinct beams includes wavelengths of about 655 nm and 1060 nm coherent light.

11. The non-invasive method of claim 6, wherein the optical radiation is applied to a selected region of dermal biological tissue to be treated by application of multiple distinct beams, each of the multiple distinct beams having a distinct path, a maximum power of 500 mw/cm², and being directed toward the selected region of dermal biological tissue such that a higher combined power is provided in the selected region of dermal biological tissue.

12. A device for treating living biological tissue characterized by a disease state, the device comprising:
   a. a power -supply;
   b. a control for the power supply;
   c. a first diode laser powered by the power supply, the first diode laser generating coherent optical radiation at a wavelength of about 655 nm±100 nm;
   d. a second diode laser powered by the power supply, the second diode laser generating coherent optical radiation at a wavelength of about 1060 nm±100 nm;
   e. means for combining the coherent optical radiation from the first diode laser and the coherent optical radiation from the second diode laser;
   f. a fiber optic delivery system, the fiber optic delivery system separating the combined optical radiation from the diode lasers into at least two beams, each of the at least two beams consisting of a portion of the combined coherent optical radiation from the first diode laser and the coherent optical radiation from the second diode laser;
   g. at least two probes, each of the at least two probes receiving a separated beam from the fiber optic delivery system; and,
   h. each of the at least two probes having a collimating lens for focusing the beam of the probe at a desired distance from the probe, whereby directing the combined focused beams at the living biological tissue characterized by the disease state inducing a quantum degeneracy state which facilitates formation or regeneration of healthy tissue.

13. The device of claim 12, further comprising a user display for monitoring operational parameters.

14. The device of claim 12, wherein the probes are handheld probes.

15. The device of claim 14, wherein each of the at least two probes deliver optical radiation at a maximum power of about 500 mw/cm².

16. The device of claim 15, wherein the biological tissue to be treated is part of an organism having a dermal layer and the tissue to be treated lies beneath the dermal layer, and wherein the at least two probes may be coordinated by orientation and arrangement to direct optical radiation to the tissue to be treated but impinge on separate areas of dermal layer.

17. The device of claim 15, wherein the biological tissue to be treated is part of the dermal layer of an organism, and wherein the at least two probes may be coordinated by orientation and arrangement to direct optical radiation to impinge upon and combine at the biological tissue to be treated at the dermal layer.

18. The device of claim 12 and further comprising:
   a. a third diode laser powered by the power supply, the third diode laser generating coherent optical radiation at a third wavelength, the third wavelength being distinct from the wavelengths of the first and second diode lasers and wherein the coherent optical radiation at a third wavelength is combined with the coherent optical radiation from the first and second diode lasers.

19. The device of claim 12 and wherein the lasers are controlled by modulating optical output of the lasers with modulation frequencies between about 0.1 hertz to about 100 kilohertz.

20. A non-invasive treatment process for living biological tissue characterized by a disease state, the treatment process comprising the steps of:
   a. identifying a first component of a subcellular structure of the living biological tissue to be treated;
   b. selected a first wavelength of coherent light, the selected wavelength corresponding to a primary absorption wavelength or primary excitation frequency of a chemical present in the first component of the subcellular structure;
   c. providing a diode laser for generating coherent light at the first wavelength;
   d. selecting a second wavelength of coherent light, the selected wavelength corresponding to another absorption wavelength or another excitation frequency of the chemical present in the first component of the subcellular structure;
   e. providing a diode laser for generating coherent light at the second selected wavelength;
   f. combining the coherent light generated from the diode laser at the first wavelength and the coherent light generated from the diode laser at the second wavelength; and,
   g. applying the combined coherent light to the living biological tissue such that a quantum degeneracy state is induced which facilitates formation or regeneration of healthy tissue.

21. The non-invasive treatment process of claim 20, wherein the second wavelength is a golden mean ratio multiple of the first wavelength.

22. The non-invasive treatment process of claim 21, wherein the first wavelength is about 655 nm.

23. The non-invasive treatment process of claim 21, wherein the second wavelength is about 1060 nm.

24. The non-invasive treatment process of claim 20, further comprising the step of transmitting the combined coherent light through a fiber optic delivery system prior to the step of applying to the biological tissue.

25. The non-invasive treatment process claim 20, further comprising the step of collimating the combined coherent light prior to the step of applying to the biological tissue.

26. The non-invasive treatment process of claim 25, further comprising the step of-splitting the combined coherent light into multiple beams of combined coherent light prior to the step of applying to the biological tissue.

27. The non-invasive treatment process of claim 20 wherein activity of Heat Shock Protein 47 (HSP47) is enhanced by application of the combined coherent light in the biological tissue to be treated, such that collagen synthesis is stimulated.

28. The non-invasive treatment process of claim 20 and wherein a third coherent light of a wavelength, distinct from the first and second wavelengths, is combined with the first and second coherent lights.

29. The non-invasive treatment process of claim 28 and wherein the third coherent light has a wavelength of about $2.77\mu$.

30. The non-invasive treatment process of claim 20 and wherein the biological tissue to be treated is a dermal tissue.

31. The non-invasive treatment process of claim 30 and wherein the dermal tissue is characterized by wounds or ulcers or bedsores.

32. The non-invasive treatment process of claim 20 and further comprising:
   a. controlling the optical output of the lasers by modulating output between 0.1 hertz and 100 kilohertz.

* * * * *